United States Patent
Sato

(10) Patent No.: US 8,777,847 B2
(45) Date of Patent: Jul. 15, 2014

(54) ENDOSCOPE WITH DISTAL END COVER

(71) Applicant: Olympus Medical Systems Corp., Tokyo (JP)

(72) Inventor: Yosuke Sato, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/869,496

(22) Filed: Apr. 24, 2013

(65) Prior Publication Data

US 2013/0274554 A1 Oct. 17, 2013

Related U.S. Application Data

(63) Continuation of application No. PCT/JP2012/075942, filed on Oct. 5, 2012.

(30) Foreign Application Priority Data

Oct. 12, 2011 (JP) .................................. 2011-225200
Oct. 12, 2011 (JP) .................................. 2011-225201

(51) Int. Cl.
*A61B 1/06* (2006.01)
*A61B 1/00* (2006.01)

(52) U.S. Cl.
CPC ............... *A61B 1/06* (2013.01); *A61B 1/00096* (2013.01)
USPC .......................................... 600/177; 600/129

(58) Field of Classification Search
USPC ........................... 600/129, 130, 175, 176, 177
See application file for complete search history.

(56) References Cited

U.S. PATENT DOCUMENTS 4,671,630 A    6/1987  Takahashi
4,841,952 A *  6/1989  Sato et al. ..................... 600/129

(Continued)

FOREIGN PATENT DOCUMENTS

EP    2 546 043 A1    1/2013
JP    59-129050 A     7/1984

(Continued)

OTHER PUBLICATIONS

Extended Supplementary European Search Report dated Feb. 3, 2014 from related European Application No. 12 83 9675.1.

*Primary Examiner* — John P Leubecker
(74) *Attorney, Agent, or Firm* — Scully, Scott, Murphy & Presser, P.C.

(57) ABSTRACT

An endoscope includes a rigid portion having an illuminating portion disposed therein and a cover integrally molded to include a transparent first resin member and a colored second resin member. The first resin member configures a first molded portion including an illumination window forming portion which includes an incident surface on which the illumination light is made incident and an emission surface from which the incident illumination light is emitted and an eaves portion projecting from the illumination window forming portion and including a first surface located on the emission surface side and a second surface located on the incident surface side. The second resin member configures a second molded portion forming a cover external shape that covers, the side surface of the illumination window forming portion, the first surface of the eaves portion, and the second surface of the eaves portion.

8 Claims, 9 Drawing Sheets

(56) References Cited

U.S. PATENT DOCUMENTS

| | | | |
|---|---|---|---|
| 5,188,092 A * | 2/1993 | White | 600/167 |
| 5,536,244 A * | 7/1996 | Muller et al. | 600/176 |
| 5,951,464 A * | 9/1999 | Takahashi et al. | 600/176 |
| 7,239,782 B1 | 7/2007 | Treado et al. | |
| 2006/0106287 A1* | 5/2006 | Webler et al. | 600/176 |
| 2008/0242935 A1* | 10/2008 | Inoue | 600/176 |
| 2012/0209072 A1* | 8/2012 | Oue et al. | 600/129 |
| 2012/0323078 A1* | 12/2012 | Kikumori et al. | 600/162 |

FOREIGN PATENT DOCUMENTS

| | | |
|---|---|---|
| JP | 8-19510 A | 1/1996 |
| JP | 8-152565 A | 6/1996 |
| JP | 8-154890 A | 6/1996 |
| JP | 10-57311 A | 3/1998 |
| JP | 2002-85326 A | 3/2002 |
| JP | 2004-33587 A | 2/2004 |
| WO | 2007/133594 A2 | 11/2007 |
| WO | 2011/111242 A1 | 9/2011 |

* cited by examiner

ENDOSCOPE WITH DISTAL END COVER

CROSS REFERENCE TO RELATED APPLICATION

This application is a continuation application of PCT/JP2012/075942 filed on Oct. 5, 2012 and claims benefit of Japanese Applications No. 2011-225200 filed in Japan on Oct. 12, 2011, No. 2011-225201 filed in Japan on Oct. 12, 2011, the entire contents of each of which are incorporated herein by their reference.

BACKGROUND OF THE INVENTION

1. Field of the Invention

The present invention relates to an endoscope in which a distal end cover, which is integrally molded from a plurality of kinds of resin, is bonded and fixed to a distal end rigid portion configuring a distal end portion of an endoscope insertion portion.

2. Description of the Related Art

An endoscope is widely used in a medical field and an industrial field. In the endoscope, a target of a diagnosis or an observation is inside a living organism, plant facilities, or the like. Therefore, when an endoscopic observation is performed, a light source for illuminating an observation target is necessary.

A general endoscope device includes an endoscope and a light source device, which is an external device of the endoscope. Illumination light emitted by the light source device is supplied to a light guide provided in the endoscope. The supplied illumination light is transmitted by the light guide. The transmitted illumination light is emitted from an illumination window provided on a distal end side of an insertion portion of the endoscope and illuminates the observation target.

In general, the illumination window is water-tightly fixed to a through-hole formed in a distal end cover having insulating properties. The distal end cover, to which the illumination window is fixed, is integrally fixed to a distal end rigid portion made of metal such as stainless steel. The distal end rigid portion configures a distal end portion of the insertion portion.

In recent years, an endoscope 5 is proposed in which a distal end cover 3 is bonded and fixed, with an adhesive 4, to a distal end rigid portion 2 made of metal configuring a distal end portion 1 as shown in FIGS. 1 and 2. The distal end cover 3 is configured by, for example, integrally molding a plurality of kinds of resin using two color molding. More specifically, the distal end cover 3 is configured by integrating a first molded portion 6 and a second molded portion 7. The first molded portion 6 is formed of a transparent first resin member including an illumination window portion 6w. The second molded portion 7 is formed of a colored second resin member configuring a light blocking portion.

In the endoscope 5, illumination light transmitted by a light guide 10 is transmitted through a lens for illumination 11 and the illumination window portion 6w of the first molded portion 6 and emitted toward an observation target. Reference numeral 12 denotes an observation optical portion, reference numeral 13 denotes a lens barrel, reference numeral 14 denotes an optical member for observation, reference numeral 15 denotes a hole for treatment instrument channel, reference numeral 16 denotes a nozzle, and reference numeral 17 denotes a hole for air/water feeding. As shown in FIG. 3, cracks 9a and 9b are likely to occur on boundary surfaces 8a and 8b between the first molded portion 6 and the second molded portion 7 in a vicinity of the adhesive 4 of the distal end cover 3.

SUMMARY OF THE INVENTION

An endoscope according to an aspect of the present invention includes: a distal end rigid portion configuring a distal end portion of an endoscope insertion portion and having an illuminating portion disposed therein configured to emit illumination light; and a distal end cover fixed to the distal end rigid portion and integrally molded to include a transparent first resin member and a colored second resin member. The first resin member configures a first molded portion including an illumination window forming portion which includes an incident surface on which the illumination light emitted from the illuminating portion is made incident and an emission surface from which the incident illumination light is emitted and an eaves portion projecting from a side surface of the illumination window forming portion and including a first surface located on the emission surface side and separated from the emission surface to the incident surface side, and a second surface located on the incident surface side. The second resin member configures a second molded portion forming a distal end cover external shape that covers, in a close contact state, the side surface of the illumination window forming portion, the first surface of the eaves portion, and the second surface of the eaves portion.

An endoscope according to another aspect of the present invention includes: a distal end rigid portion configuring a distal end portion of an endoscope insertion portion and having an illuminating portion disposed therein configured to emit illumination light; and a distal end cover bonded and fixed to the distal end rigid portion and integrally molded to include a transparent first resin member and a colored second resin member. The first resin member configures a first molded portion including an illumination window forming portion which includes an incident surface on which the illumination light emitted from the illuminating portion is made incident and an emission surface from which the incident illumination light is emitted and a first concave portion provided on the incident surface side in the illumination window forming portion, in which the illuminating portion is arranged. The second resin member configures a second molded portion including a portion covering a side surface of the illumination window forming portion, a proximal end face present in a position projecting with respect to an end face on the incident surface side of the first molded portion, the proximal end face being opposed to the distal end rigid portion, and a convex portion further projecting from the distal end face. The distal end rigid portion includes a second concave portion having a bottom surface opposed to an end face around the first concave portion in the first molded portion, the second concave portion functioning as an adhesive pool, on an inside of which the convex portion is arranged.

An endoscope according to still another aspect of the present invention includes: a distal end rigid portion configuring a distal end portion of an endoscope insertion portion and having an illuminating portion disposed therein configured to emit illumination light; and a distal end cover bonded and fixed to the distal end rigid portion and integrally molded to include a transparent first resin member and a colored second resin member. The first resin member configures a first molded portion including an illumination window forming portion which includes an incident surface on which the illumination light is made incident from the illuminating portion and an emission surface from which the incident illumination light is emitted and a first concave portion provided on the incident surface side in the illumination window forming portion, in which the illuminating portion is arranged. The second resin member configures a second molded portion including a portion covering a side surface of the illumination window forming portion and a proximal end face present in a position projecting with respect to an end face on the incident surface side of the first molded portion, the proximal end face being opposed to the distal end rigid portion. The distal end rigid portion includes a convex portion projecting toward an end face around the first concave portion to arrange a distal end face in a position spaced apart from the end face around the first concave portion in the first molded portion, the convex portion preventing an adhesive from intruding into a boundary surface between the first molded portion and the second molded portion.

BRIEF DESCRIPTION OF THE DRAWINGS

FIG. 1 is a front view of an endoscope in which a distal end cover molded by two color molding is bonded and fixed to a distal end rigid portion.

FIG. 2 is a sectional view taken along line Y2-Y2 of FIG. 1.

FIG. 3 is a diagram for explaining a configuration of an integrally formed distal end cover and cracks that occur on a boundary surface between a first molded portion and a second molded portion of the distal end cover.

FIG. 4 is a front view of an endoscope in which a distal end cover molded by two color molding is bonded and fixed to a distal end rigid portion.

FIG. 5 is a sectional view taken along line Y5-Y5 of FIG. 4.

FIG. 6 is an enlarged view of a portion indicated by an arrow Y6 in FIG. 5 and a diagram for explaining a configuration of an integrally formed distal end cover and cracks that occur on a boundary surface between a first molded portion and a second molded portion of the distal end cover.

FIG. 8 is a front view of an endoscope in which the distal end cover molded by the two color molding is bonded and fixed to a distal end rigid portion.

FIG. 9 is a sectional view taken along line Y9-Y9 of FIG. 8 and a diagram for explaining a distal end cover in which a distal end cover proximal end face is configured by a first molded portion and a second molded portion.

FIG. 10 is a sectional view taken along line Y9-Y9 of FIG. 8 and a diagram for explaining a distal end cover in which a distal end cover proximal end face is configured by a second molded portion.

FIG. 11 is a front view of an endoscope in which a distal end cover molded by two color molding is bonded and fixed to a distal end rigid portion.

FIG. 12 is a sectional view taken along line Y12-Y12 of FIG. 11 and a diagram for explaining a configuration and action of an integrally molded distal end cover.

DETAILED DESCRIPTION OF THE PREFERRED EMBODIMENTS

Embodiments of the present invention are explained below with reference to the drawings.

A configuration and action of a distal end cover included in an endoscope according to a first embodiment are explained with reference to FIGS. 4 to 6.

Figure 1:
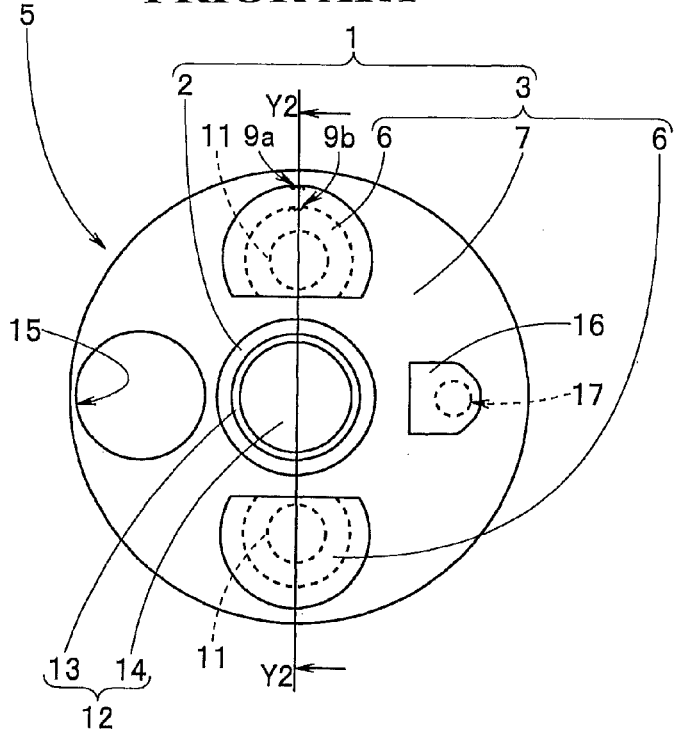
FIGS. 1 to 3 relate to a related art.
Figure 2:
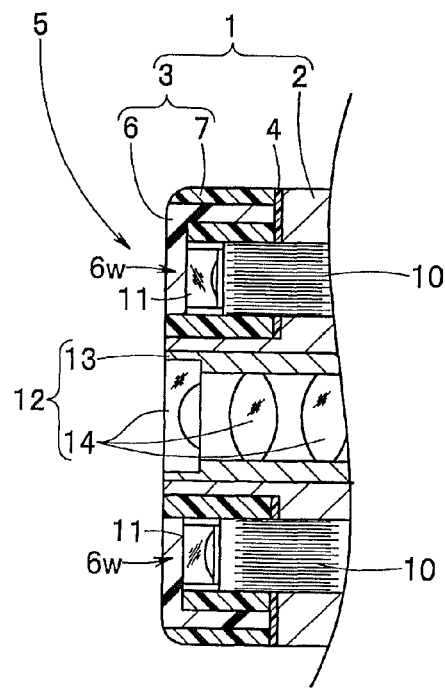
Figure 3:
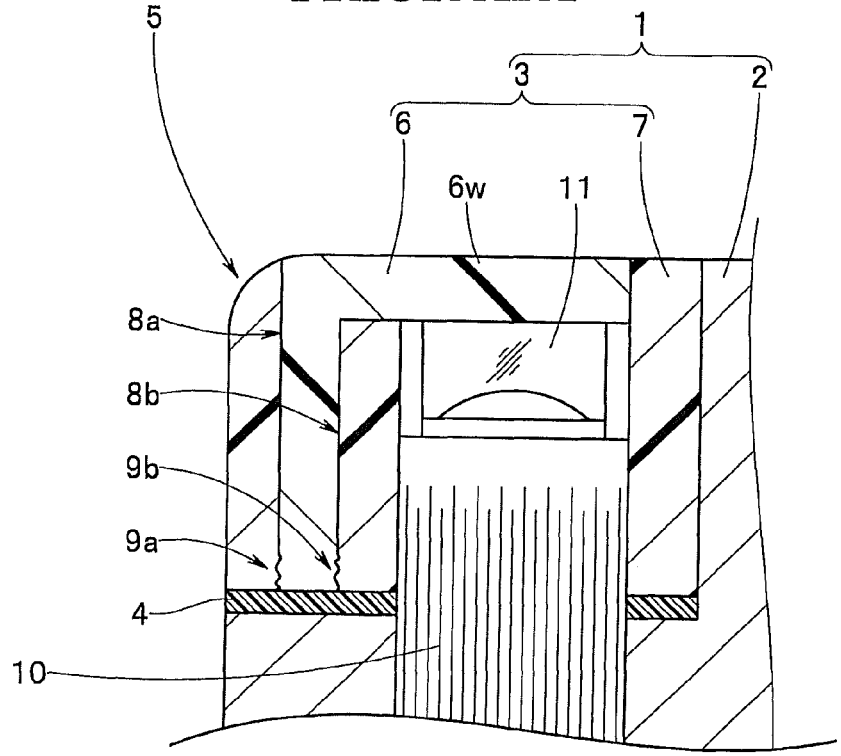
Figure 4:
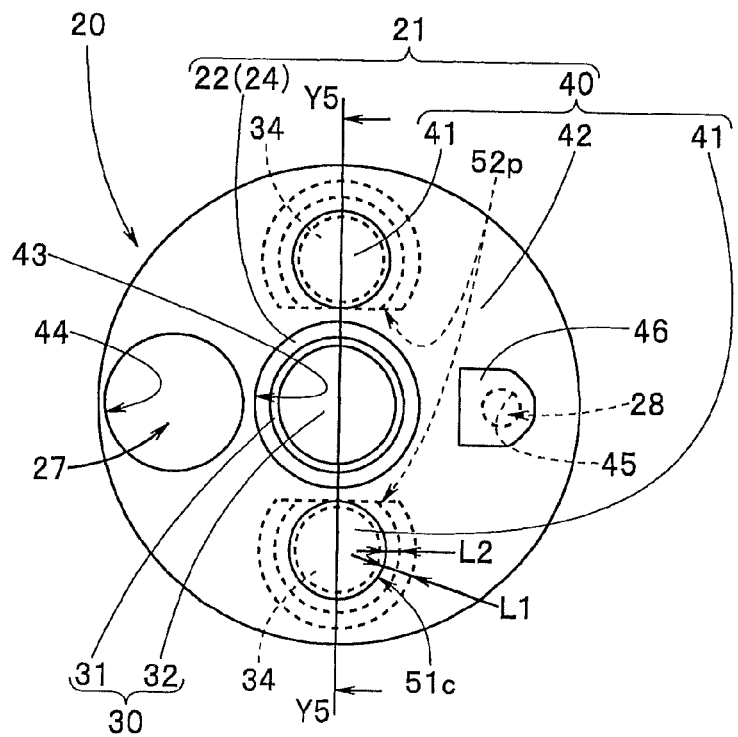
FIGS. 4 to 6 relate to a first embodiment of the present invention.
Figure 5:
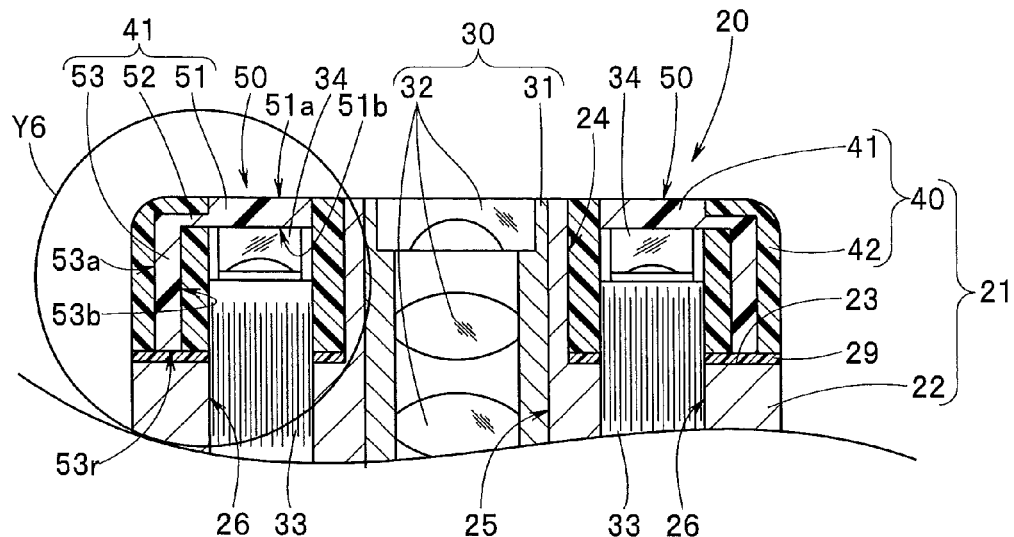

As shown in FIGS. 4 and 5, an insertion portion distal end portion 21 of an endoscope 20 is configured to mainly include a distal end cover 40 and a distal end rigid portion 22.

The distal end rigid portion 22 is a cylinder made of metal such as stainless steel. The distal end rigid portion 22 includes a bonding surface 23 and a center convex portion 24. The center convex portion 24 projects from the bonding surface 23 by height set in advance. The height of the center convex portion 24 corresponds to a thickness dimension of the distal end cover 40. In this embodiment, the distal end cover 40 is bonded and fixed to the bonding surface 23 of the distal end rigid portion 22 with an adhesive. Reference numeral 29 denotes the adhesive.

In the distal end rigid portion 22, for example, a hole for lens barrel 25, a pair of holes for light guide 26, a treatment instrument channel hole 27, and a hole for air/water feeding 28 are formed. A lens barrel 31 is arranged in the hole for lens barrel 25. Optical members such as a plurality of lenses 32 configuring an objective optical system 30 are disposed in the lens barrel 31. A light guide fiber bundle 33 configuring an illuminating portion is inserted through the holes for light guide 26. Reference numeral 34 denotes a lens for illumination. The lens for illumination 34 is bonded and fixed to a distal end face of the light guide fiber bundle 33 with an optical adhesive.

The respective holes 25, 26, 27, and 28 are through-holes. Each of center axes of the respective holes 25, 26, 27, and 28 is parallel to a longitudinal axis of the distal end rigid portion 22.

The distal end cover 40 is configured to integrally include a first molded portion 41 and a second molded portion 42. The first molded portion 41 is molded from a transparent first resin member having insulating properties and configures an optical portion. The second molded portion 42 is molded from a colored second resin member having insulating properties and configures a light blocking portion.

Figure 6:
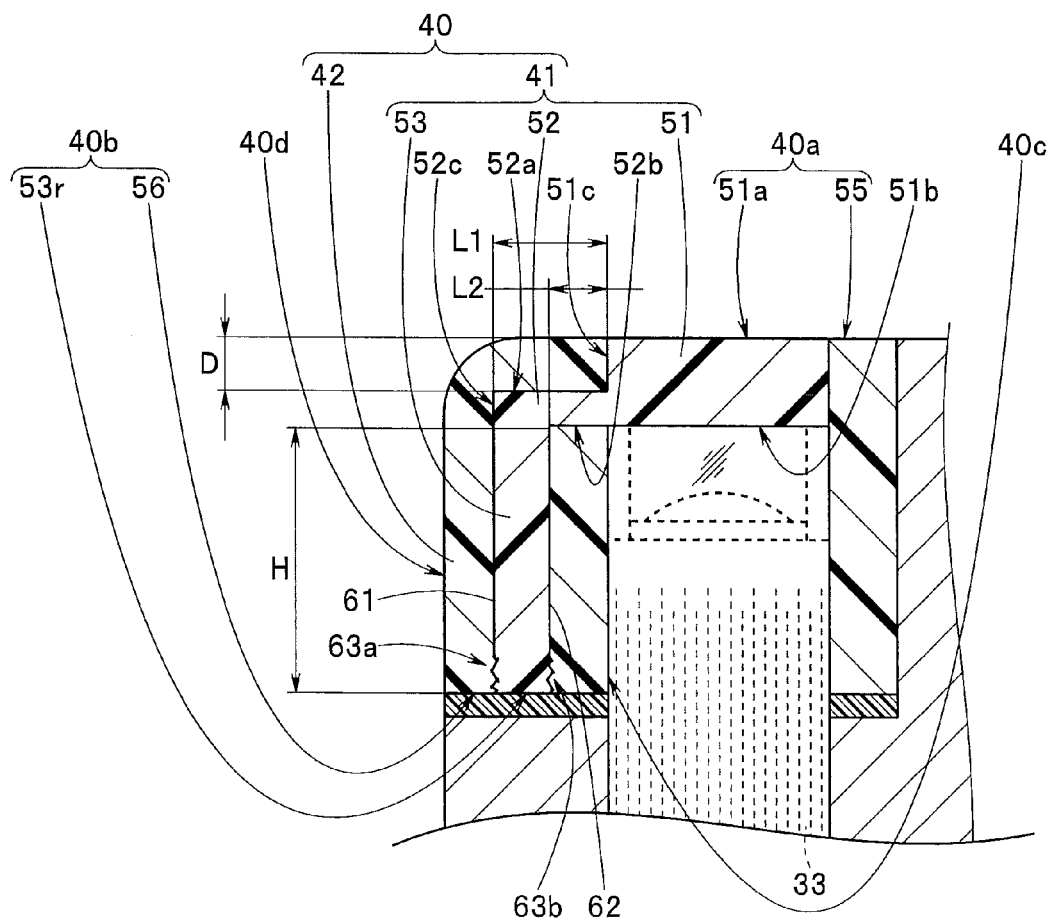

As shown in FIG. 6, the distal end cover 40 includes a distal end cover distal end face 40a, a distal end cover proximal end face 40b, an illuminating portion arrangement space 40c, and a distal end cover side surface 40d. The illuminating portion arrangement space 40c includes an opening on the distal end cover proximal end face 40b. A distal end portion of the light guide fiber bundle 33 and the lens for illumination 34 are disposed in the illuminating portion arrangement space 40c.

In this embodiment, the first molded portion 41 is exposed and provided as an illumination window portion 50 on the distal end cover distal end face 40a of the distal end cover 40.

In the second molded portion 42 configuring the distal end cover 40, a center through-hole 43, a through-hole for treatment instrument channel 44, and a through-hole for water feeding 45 are formed. The center convex portion 24 of the distal end rigid portion 22 is arranged in the center through-hole 43. The through-hole for treatment instrument channel 44 is arranged to communicate with the treatment instrument channel hole 27 of the distal end rigid portion 22. The through-hole for water feeding 45 is arranged to communicate with the hole for air/water feeding 28 of the distal end rigid portion 22.

Reference numeral 46 denotes a cleaning nozzle. A nozzle ejection port (not shown in the figure) of the cleaning nozzle 46 is arranged to face the lenses 32 configuring an observation window of the objective optical system 30. The cleaning nozzle 46 is separated from the distal end cover 40. The cleaning nozzle 46 is integrally fixed to the distal end cover 40 by bonding. Alternatively, the cleaning nozzle 46 may be firmly fixed to the distal end rigid portion 22 by a not-shown screw or the like.

Note that the cleaning nozzle 46 may be integrally configured with the distal end cover 40.

The illuminating portion is not limited to configurations of the light guide fiber bundle 33 and the illumination lens 34. The illuminating portion may be, for example, a light emitting element of a light emitting diode. When the illuminating portion is the light emitting diode, the light emitting diode is disposed in the illuminating portion arrangement space 40c.

As shown in FIGS. 4 to 6, the first molded portion 41 includes an illumination window forming portion 51, an eaves portion 52, and a convex portion 53. The illumination window forming portion 51 is, for example, a columnar shape portion having a diameter dimension set in advance. A distal end face of the illumination window forming portion 51 configures an emission surface 51a. A proximal end face of the illumination window forming portion 51 configures an incident surface 51b.

The eaves portion 52 is a projection projecting toward an outer side from a center of the insertion portion distal end portion 21. The eaves portion 52 projects from a side surface 51c of the illumination window forming portion 51 by an amount set in advance (a dimension L1 shown in FIGS. 4 and 6). In this embodiment, a part on the center through-hole 43 side of the eaves portion 52 is configured as a notched surface 52p having a flat shape.

The eaves portion 52 includes a first surface 52a and a second surface 52b. The eaves portion 52 is configured at thickness set in advance. The first surface 52a is located on the emission surface 51a side. The first surface 52a and the second surface 52b are parallel to each other. The first surface 52a is provided in a position a distance set in advance (a dimension D shown in FIG. 6) apart from the emission surface 51a. That is, the emission surface 51a and the first surface 52a form a step. In this embodiment, the second surface 52b is configured as a plane identical to the incident surface 51b.

The convex portion 53 projects from the second surface 52b of the eaves portion 52. The convex portion 53 projects by height set in advance and is set to thickness set in advance. An outer side surface 53a of the convex portion 53 is provided along an edge portion 52c of the eaves portion 52. An inner side surface 53b of the convex portion 53 is a distance set in advance (a dimension L2 shown in FIGS. 4 and 6) apart from the side surface 51c of the illumination window forming portion 51.

In this embodiment, a convex portion proximal end face 53r, which is a proximal end face of the convex portion 53, is set to a projecting dimension (height H shown in FIG. 6) to configure a bonding surface.

On the other hand, the second molded portion 42 forms the distal end cover 40, which has a shape set in advance shown in FIGS. 4 and 5, to cover a periphery of the first molded portion 41.

More specifically, as shown in FIG. 6, the second molded portion 42 adheres to the side surface 51c of the illumination window forming portion 51 of the first molded portion 41, the first surface 52a and the second surface 52b of the eaves portion 52, and the outer side surface 53a and the inner side surface 53b, which are side surfaces of the convex portion 53. The second molded portion 42 is formed at a thickness dimension set in advance.

As a result, the distal end cover distal end face 40a of the distal end cover 40 is configured by a distal end face 55 and the emission surface 51a. The distal end face 55 is formed by the second molded portion 42. The emission surface 51a is formed by the first molded portion 41. The emission surface 51a and the distal end face 55 configure an identical plane or a curved surface. In this embodiment, the distal end cover distal end face 40a is a plane.

The distal end cover proximal end face 40b of the distal end cover 40 is configured by a proximal end face 56 and the convex portion proximal end face 53r. The proximal end face 56 is formed by the second molded portion 42. The convex portion proximal end face 53r is formed by the first molded portion 41. The convex portion proximal end face 53r and the proximal end face 56 configure an identical plane.

The illuminating portion arrangement space 40c and the distal end cover side surface 40d are formed by the second molded portion 42. A bottom surface of the illuminating portion arrangement space 40c is the incident surface 51b. A diameter dimension of the incident surface 51b is set by forming the second molded portion 42.

The distal end cover 40 configured as explained above is integrally fixed to the distal end rigid portion 22 with the adhesive 29. More specifically, first, the distal end cover proximal end face 40b of the distal end cover 40 is brought into contact with the bonding surface 23 of the distal end rigid portion 22. Next, the adhesive 29 is caused to intrude into a gap between the distal end cover proximal end face 40b and the bonding surface 23 to bond and fix the distal end cover 40 and the distal end rigid portion 22. Alternatively, the adhesive 29 is applied on the bonding surface 23 in advance and the distal end cover proximal end face 40b is pressed against the bonding surface 23 to bond and fix the distal end cover 40 and the distal end rigid portion 22.

In the endoscope 20 having the configuration of this embodiment, as shown in FIG. 6, the second molded portion 42 is provided on a distal end face side extended line of a first boundary surface 61. The first molded portion 41 is provided on a distal end face side extended line of a second boundary surface 62. In other words, the boundary surfaces 61 and 62 are formed to be bent.

As a result, when a crack 63a occurs on the boundary surface 61 between the first molded portion 41 and the second molded portion 42 in a vicinity of the adhesive 29, it is possible to prevent, with the second molded portion 42 on the extended line, the crack 63a from leading to a fracture extending from the distal end cover proximal end face 40b to the distal end cover distal end face 40a.

On the other hand, when a crack 63b occurs on the boundary surface 62 between the first molded portion 41 and the second molded portion 42, like the second molded portion 42, it is possible to prevent, with the first molded portion 41 on the extended line, the crack 63b from leading to a fracture.

In the endoscope 20 in this embodiment, the inner side surface 53b of the convex portion 53, which is the second boundary surface 62, is provided a distance set in advance apart from the side surface 51c of the illumination window forming portion 51. In addition, the second molded portion 42, which is the light blocking portion, is provided on an extended line of the first boundary surface 61 and on an extended line of the second boundary surface 62.

As a result, the boundary surfaces 61 and 62 are arranged directly under the distal end face 55 formed by the second molded portion 42. Therefore, it is possible to substantially reduce user's visual recognition of the cracks 63a and 63b that occur on the boundary surfaces 61 and 62.

According to these configurations, it is possible to surely prevent a crack from leading to a fracture and eliminate uneasiness given to the user due to the occurrence of the crack.

Note that, in the embodiment explained above, the distal end cover proximal end face 40b is configured by the proximal end face 56 and the convex portion proximal end face 53r.

Figure 7:
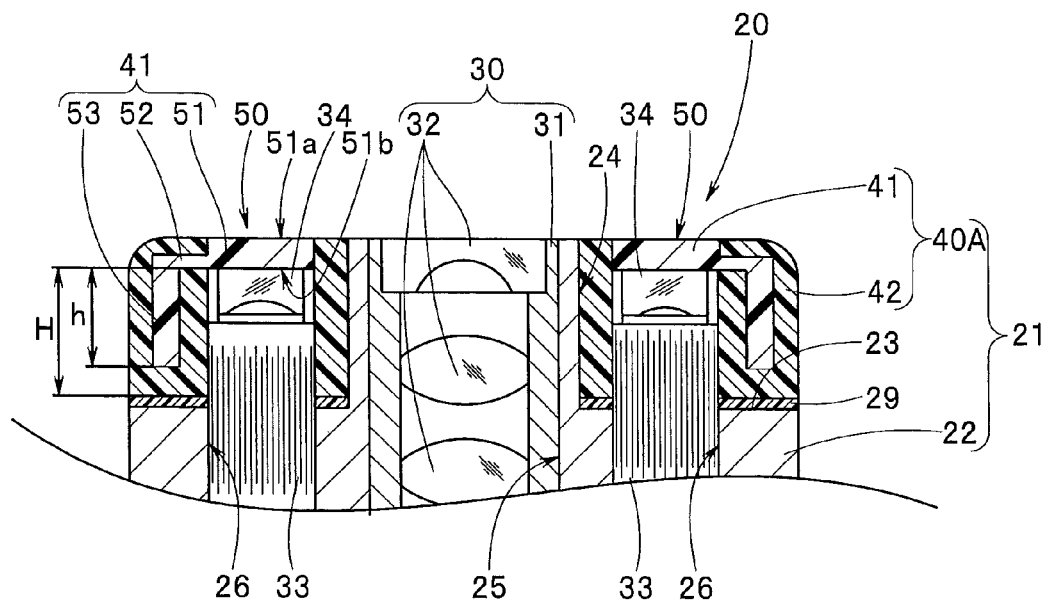
FIG. 7 is a diagram for explaining another configuration example of the distal end cover molded by the two color molding.

However, the distal end cover proximal end face 40b may be configured like a distal end cover 40A shown in FIG. 7. In the distal end cover 40A, height of the convex portion 53 of the first molded portion 41 is set to h lower than height H of the convex portion 53 of the distal end cover 40. The second molded portion 42 is provided to be closely attached to the convex portion proximal end face 53r of the convex portion 53 and at thickness set in advance.

As a result, in the distal end cover 40A, the distal end cover proximal end face 40b is configured by the second molded portion 42. Therefore, the boundary surfaces 61 and 62 are configured to be separated from the adhesive 29. As a result, it is possible to eliminate occurrence of cracks on the boundary surfaces 61 and 62 dues to the adhesive 29.

In the embodiment explained above, the first surface 52a and the second surface 52b of the eaves portion 52 are set in a parallel relation and the second surface 52b is set as a plane identical with the incident surface 51b. However, as long as the eaves portion 52 has the thickness set in advance, the eaves portion 52 may be configured such that the second surface 52b forms a step portion with the incident surface 51b or configured such that the second surface 52b is an inclined surface, a curved surface, or the like.

Figure 8:
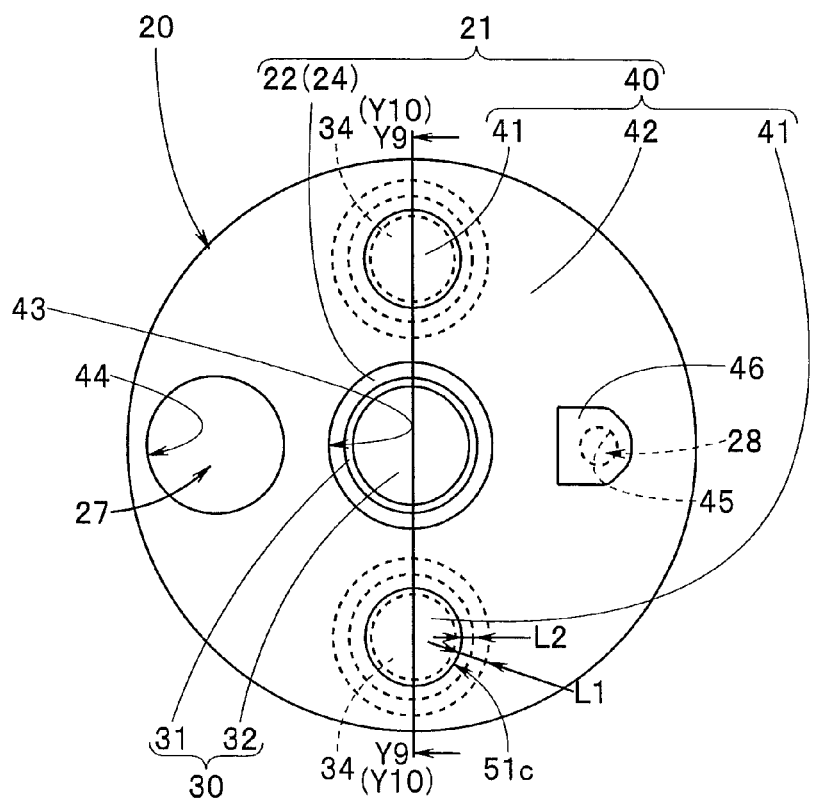
FIGS. 8 to 10 are diagrams for explaining still another configuration example of the distal end cover molded by the two color molding.
Figure 9:
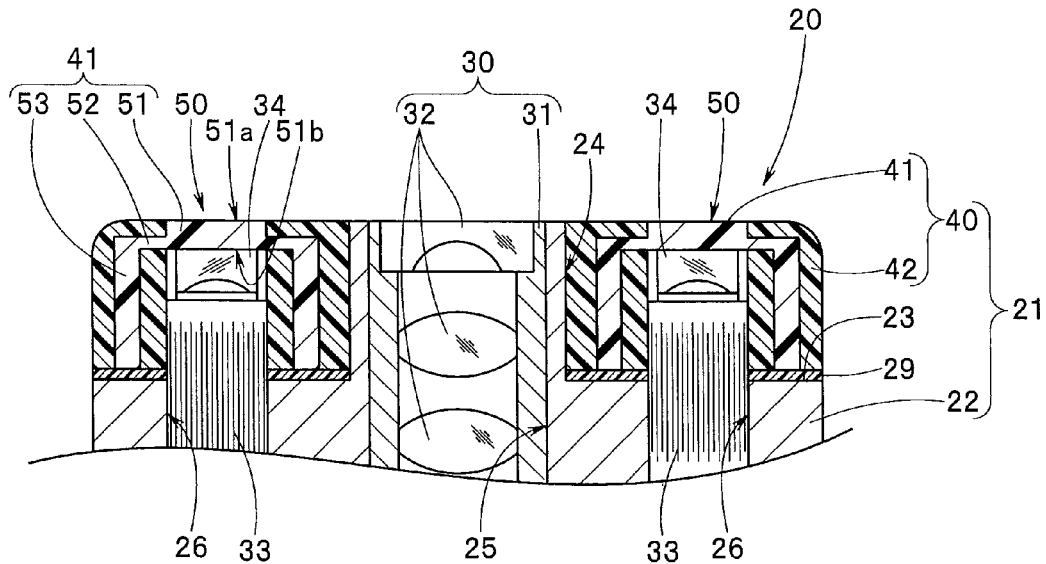
Figure 10:
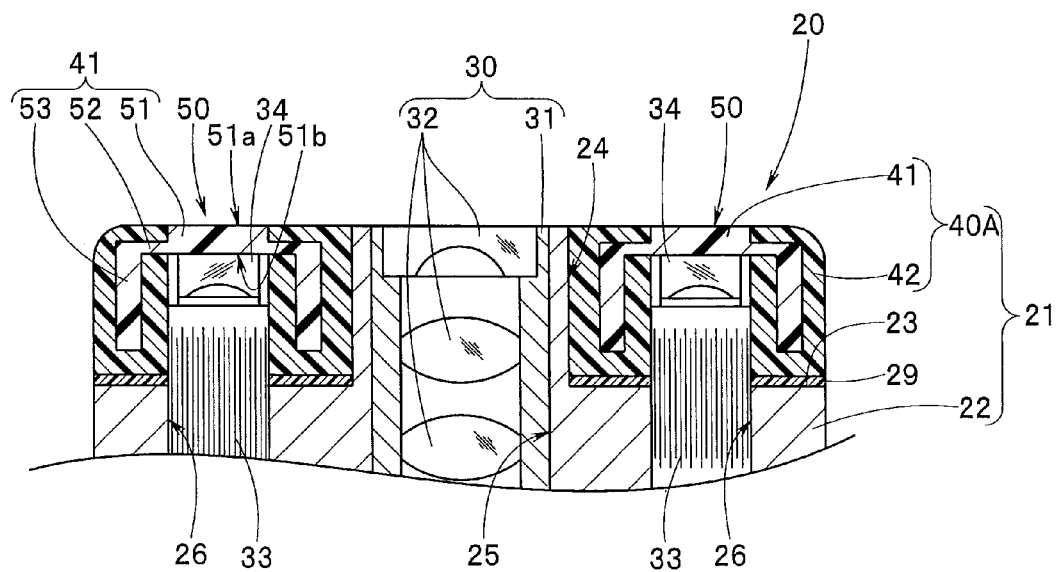

In the embodiment explained above, the notched surface 52p having the flat shape is provided in a part on the center through-hole 43 side of the eaves portion 52. However, as shown in FIG. 8, the eaves portion 52 may be configured in a circular shape without providing the notched surface 52p in the eaves portion 52. In other words, as shown in FIGS. 9 and 10, the first molded portion 41 may be configured in a cylindrical shape.

A second embodiment of the present invention is explained below with reference to the drawings.

A configuration and action of a distal end cover included in an endoscope are explained with reference to FIGS. 11 and 12.

Figure 11:
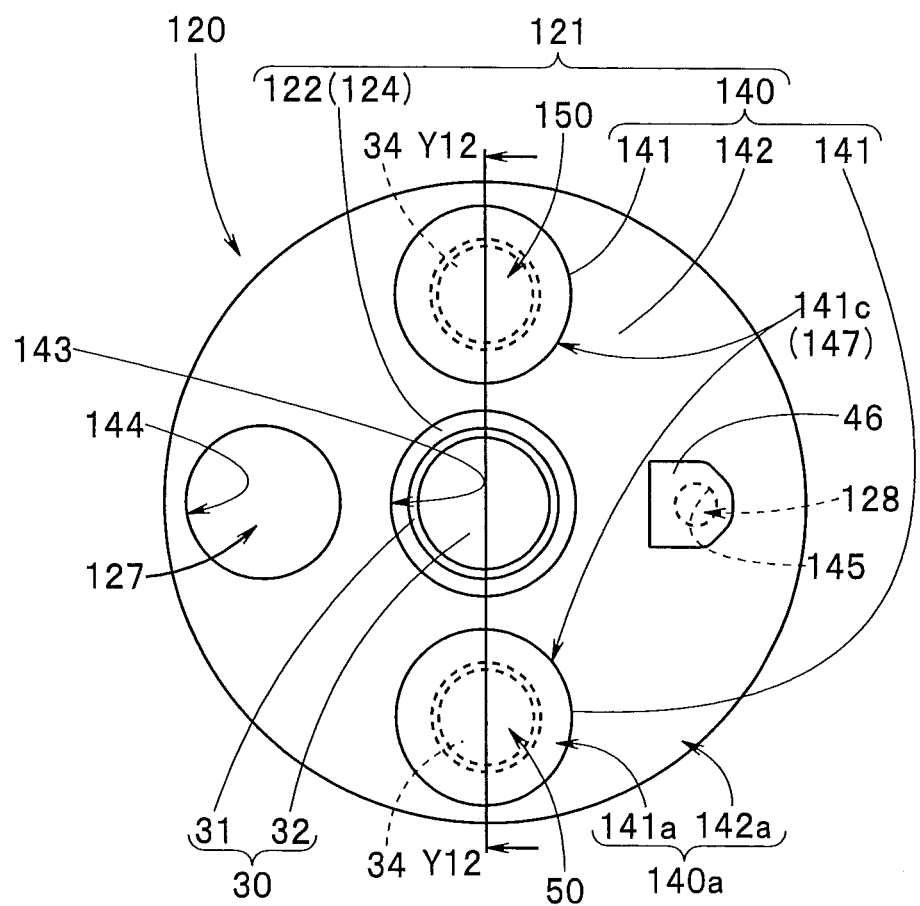
FIGS. 11 and 12 relate to a second embodiment of the present invention.
Figure 12:
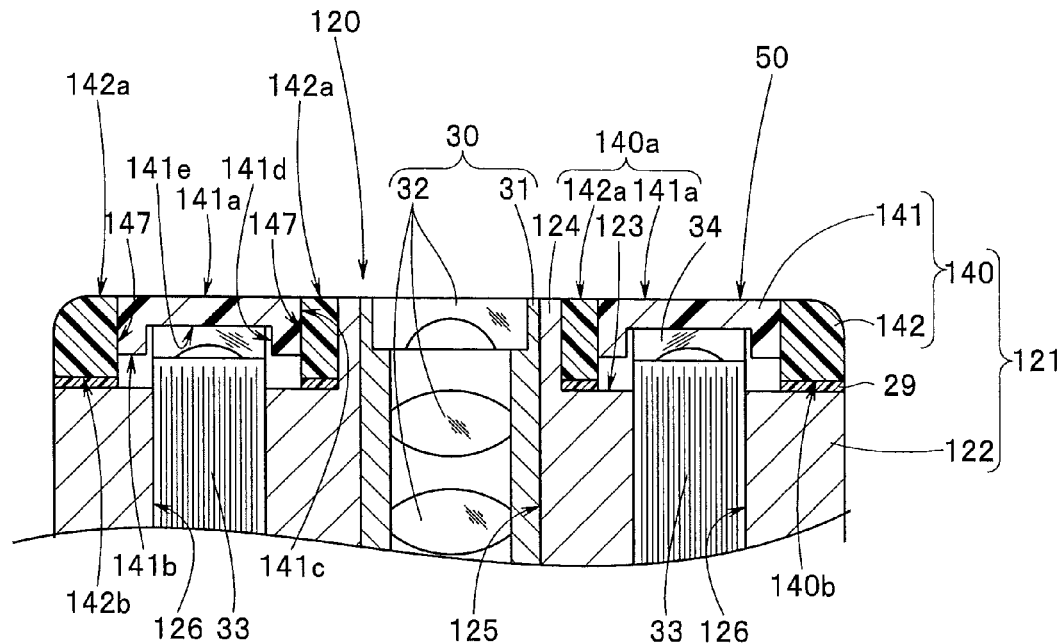

As shown in FIGS. 11 and 12, an insertion portion distal end portion 121 of an endoscope 120 in this embodiment is configured to mainly include a distal end cover 140 and a distal end rigid portion 122.

The distal end rigid portion 122 is a cylinder made of metal such as stainless steel. The distal end rigid portion 122 includes a distal end face 123 and a center convex portion 124. The center convex portion 124 projects from the distal end face 123 by height set in advance. The height of the center convex portion 124 corresponds to a thickness dimension of the distal end cover 140. In this embodiment, the distal end cover 140 is bonded and fixed to the distal end face 123, which is configured by a plane of the distal end rigid portion 122, with an adhesive. Reference numeral 29 denotes the adhesive.

In this embodiment, in the distal end rigid portion 122, for example, a hole for lens barrel 125, a pair of holes for light guide 126, a treatment instrument channel hole 127, and a hole for air/water feeding 128 are formed. The respective holes 125, 126, 127, and 128 are through-holes. Each of center axes of the respective holes 125, 126, 127, and 128 is parallel to a longitudinal axis of the distal end rigid portion 122.

Note that, in this embodiment, when an illuminating portion is a light emitting diode, the light emitting diode is disposed in a concave portion 141d.

The distal end cover 140 is configured to integrally include a first molded portion 141 and a second molded portion 142. The first molded portion 141 is molded from a transparent first resin member having insulating properties. The second molded portion 142 is molded from a colored second resin member having insulating properties and configuring a light blocking portion. Reference numeral 150 denotes an illumination window portion.

The first molded portion 141 has, for example, a columnar shape. The first molded portion 141 includes a first molded portion distal end face (hereinafter described as first distal end face) 141a and a first molded portion proximal end face (hereinafter described as first proximal end face) 141b. The first distal end face 141a is arranged to be exposed to a distal end cover distal end face 140a of the distal end cover 140 explained above and configures the illumination window portion 150. Reference sign 141c denotes a side surface. In this embodiment, a side surface 141c is an external circumferential surface.

In the first molded portion 141, a concave portion 141d having an opening on the first proximal end face 141b is formed. The lens for illumination 34 is arranged in the concave portion 141d. A bottom surface 141e of the concave portion 141d is configured as an incident surface. Illumination light emitted from the lens for illumination 34 is made incident on the incident surface.

The second molded portion 142 configuring the distal end cover 140 forms an external shape of the distal end cover 140. The second molded portion 142 is provided to be closely attached to the side surface 141c of the first molded portion 141.

In this embodiment, a second molded portion distal end face (hereinafter described as second distal end face) 142a of the second molded portion 142 configures the distal end cover distal end face 140a of the distal end cover 140 in conjunction with the first distal end face 141a of the first molded portion 141. The first distal end face 141a and the second distal end face 142a configure an identical plane or curved surface of the distal end cover distal end face 140a. In this embodiment, the distal end cover distal end face 140a is a plane.

A second molded portion proximal end face (hereinafter described as second proximal end face) 142b of the second molded portion 142 projects with respect to the first proximal end face 141b by height set in advance. That is, in this embodiment, a distal end cover proximal end face 140b of the distal end cover 140 is configured by the second proximal end face 142b.

The second molded portion 142 is configured to include a center through-hole 143, a through-hole for treatment instrument channel 144, and a through-hole for water feeding 145. The center convex portion 124 of the distal end rigid portion 122 is arranged in the center through-hole 143. The through-hole for treatment instrument channel 144 is arranged to communicate with the treatment instrument channel hole 127 of the distal end rigid portion 122. The through-hole for water feeding 145 is arranged to communicate with the hole for air/water feeding 128 of the distal end rigid portion 122.

Reference numeral 147 denotes a boundary surface between the first molded portion 141 and the second molded portion 142.

The endoscope 120 in this embodiment is configured by fixing the second proximal end face 142b of the second molded portion 142 and the distal end face 123 of the distal end rigid portion 122 with the adhesive 29. More specifically, first, the second proximal end face 142b of the distal end cover 140 is brought into contact with the distal end rigid portion 122. Next, the adhesive 29 is caused to intrude into a gap between the second proximal end face 142b and the distal end face 123 to bond and fix the distal end cover 140 to the distal end rigid portion 122. Alternatively, the adhesive 29 is applied on the distal end face 123 and the second proximal end face 142b of the distal end cover 140 is pressed against the distal end face 123 of the distal end rigid portion 122 to bond and fix the distal end cover 140 and the distal end rigid portion 122.

In this embodiment, the second proximal end face 142b of the second molded portion 142 further projects than the first proximal end face 141b of the first molded portion 141 by height set in advance. In other words, the first proximal end face 141b and the second proximal end face 142b are configured as different surfaces separated by a step.

According to this configuration, a bonding surface between the distal end rigid portion 122 and the distal end cover 140 is configured by the second proximal end face 142b of the second molded portion 142 and the distal end face 123 of the distal end rigid portion 122. As a result, a deficiency in which stress caused in the distal end cover 140 by distortion due to hardening shrinkage of the adhesive 29 is transmitted to the boundary surface 147 between the first molded portion 141 and the second molded portion 142 to cause a crack is eliminated.

When the second proximal end face 142b is bonded and fixed to the distal end face 123, the extra adhesive 29 is prevented from adhering to the first proximal end face 141b of the first molded portion 141 climbing over the step having height set in advance.

Figure 13:
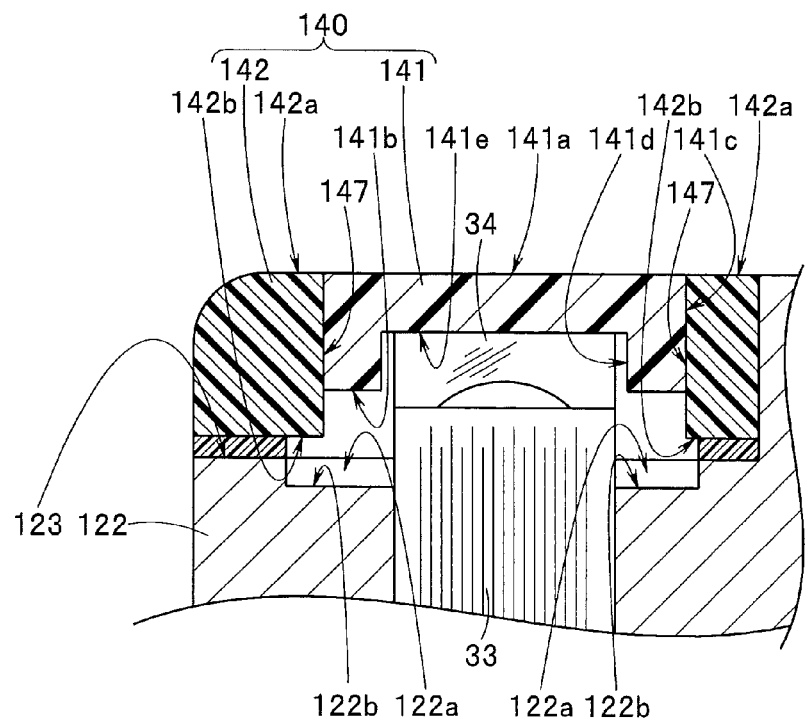
FIG. 13 is a diagram for explaining a configuration and action of an endoscope in which a distal end cover, in which a second proximal end face of a second molded portion further projects than a first proximal end face of a first molded portion by height set in advance, is bonded and fixed to a distal end rigid portion, on a distal end face of which a concave portion functioning as an adhesive pool is provided.

Note that, as shown in FIG. 13, a concave portion 122a functioning as an adhesive pool is provided in the distal end rigid portion 122. The concave portion 122a is configured in a position set in advance of the distal end face 123 in a shape set in advance. A bottom surface 122b of the concave portion 122a is provided to be opposed to the boundary surface 147 side of the second proximal end face 142b and the first proximal end face 141b of the first molded portion 141. A depth dimension of the concave portion 122a is set to a depth dimension set in advance taking into account an application amount of the adhesive 29.

According to this configuration, when the second proximal end face 142b of the second molded portion 142 and the distal end face 123 of the distal end rigid portion 122 are fixed with the adhesive 29, the extra adhesive 29 is pooled in the concave portion 122a. As a result, it is possible to surely prevent the adhesive 29 from flowing and adhering to the first proximal end face 141b of the first molded portion 141 separated by the step. Therefore, occurrence of a crack on the boundary surface 147 due to the adhesive 29 is eliminated.

Figure 14:
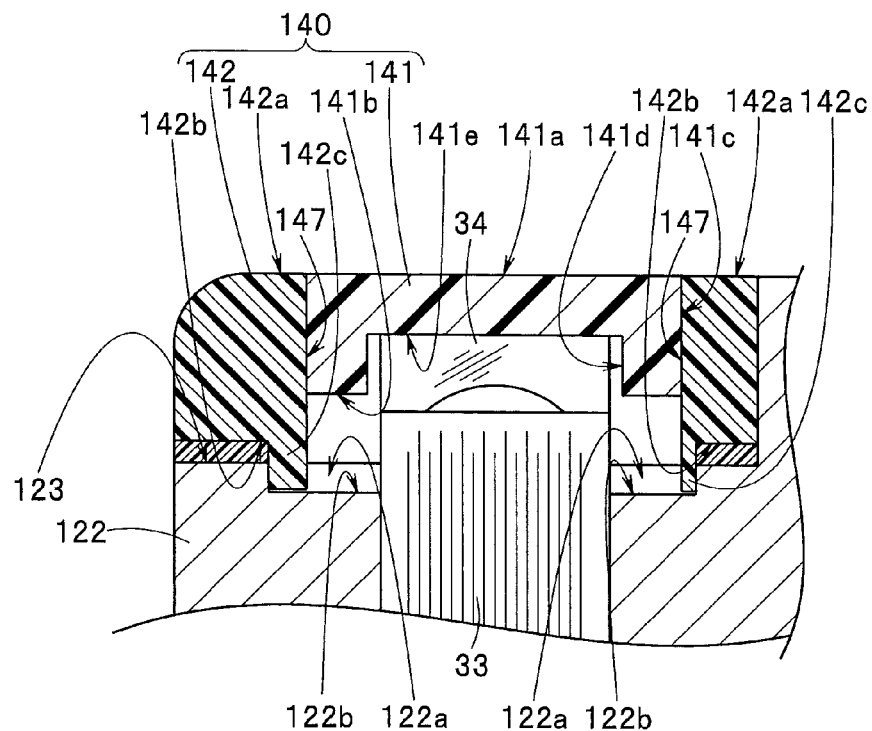
FIG. 14 is a diagram for explaining a configuration and action of an endoscope including a distal end rigid portion, on a distal end face of which a concave portion is provided, and a distal end cover in which a cover side convex portion arranged to be closely attached to a side surface of the concave portion is provided on a distal end face of a second molded portion.

In the configuration in which the concave portion 122a is provided on the distal end face 123 of the distal end rigid portion 122, a cover side convex portion 142c shown in FIG. 14 may be provided. The cover side convex portion 142c further projects than the second proximal end face 142b of the second molded portion 142 by an amount set in advance. The cover side convex portion 142c is disposed in the concave portion 122a and arranged to be closely attached to a side surface of the concave portion 122a.

According to this configuration, it is possible to prevent, with the cover side convex portion 142c, the adhesive 29 from intruding into the concave portion 122a side. As a result, adhesion of the adhesive to the first proximal end face 141b is eliminated. Occurrence of a crack on the boundary surface 147 due to the adhesive 29 is also eliminated.

Figure 15:
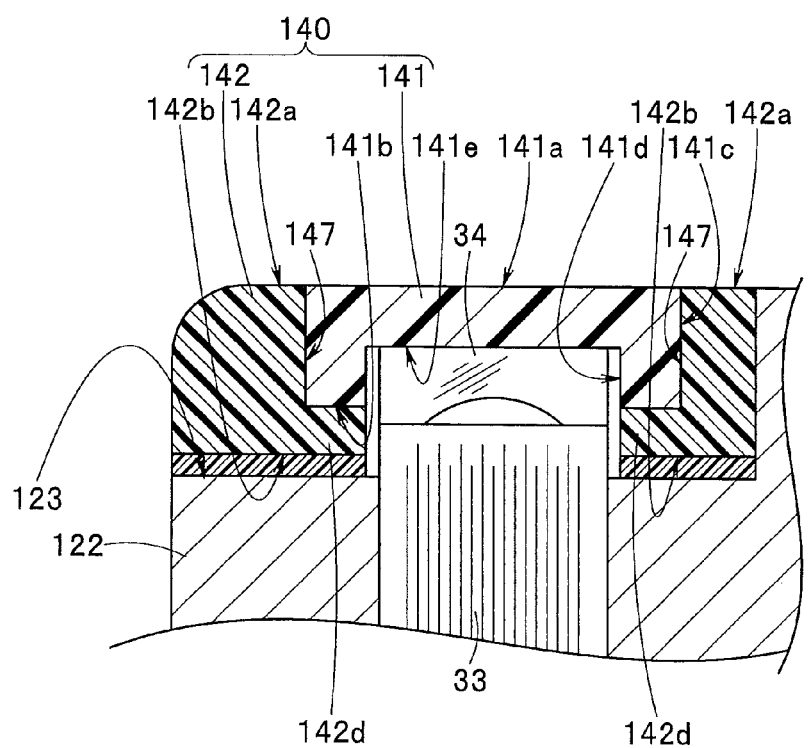
FIG. 15 is a diagram for explaining a configuration and action of an endoscope including a distal end cover in which a covering portion for covering a first proximal end face of a first molded portion is provided in a second molded portion.

As shown in FIG. 15, the second molded portion 142 may be provided with a covering portion 142d having a thickness dimension set in advance closely attached to the first proximal end face 141b side in addition to the side surface 141c side of the first molded portion 141 configuring the distal end cover 140. In this configuration, the concave portion 122a functioning as the adhesive pool may be provided on the distal end face 123 of the distal end rigid portion 122 or may be unnecessary.

According to this configuration, it is possible to cover the first proximal end face 141b of the first molded portion 141 with the covering portion 142d of the second molded portion 142 and prevent adhesion of the adhesive 29 to the first proximal end face 141b. As a result, the adhesion of the adhesive 29 to the first proximal end face 141b is eliminated and occurrence of a crack on the boundary surface 147 due to the adhesive 29 is also eliminated.

Figure 16:
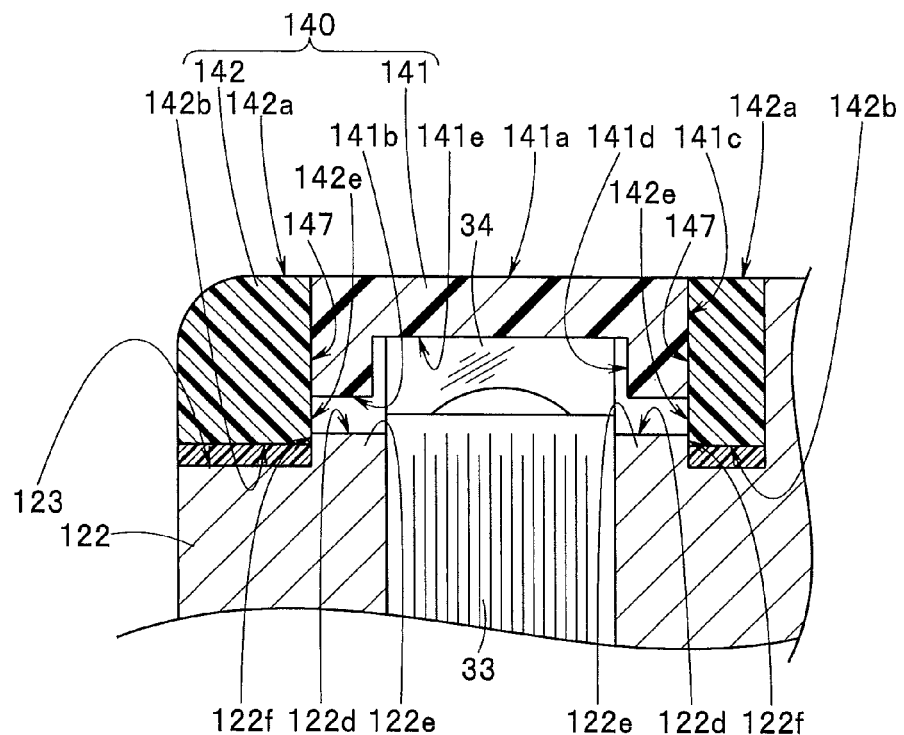
FIG. 16 is a diagram for explaining a configuration and action of an endoscope in which a convex portion side surface of a distal end rigid portion convex portion projecting from a distal end face adheres to an inner side surface of a distal end cover.

As shown in FIG. 16, a distal end rigid portion convex portion 122e may be provided on the distal end face 123 of the distal end rigid portion 122. The distal end rigid portion convex portion 122e includes a convex portion distal end face 122d opposed to the first proximal end face 141b of the first molded portion 141. The convex portion distal end face 122d projects from the distal end face 123 to be arranged a distance set in advance apart from the first proximal end face 141b. A convex portion side surface 122f of the distal end rigid portion convex portion 122e is arranged to be closely attached to an inner side surface 142e.

According to this configuration, it is possible to prevent, with the distal end rigid portion convex portion 122e, the adhesive 29 from intruding into the first proximal end face 141b side. As a result, adhesion of the adhesive to the first proximal end face 141b is eliminated and occurrence of a crack on the boundary surface 147 due to the adhesive 29 is also eliminated.

Figure 17:
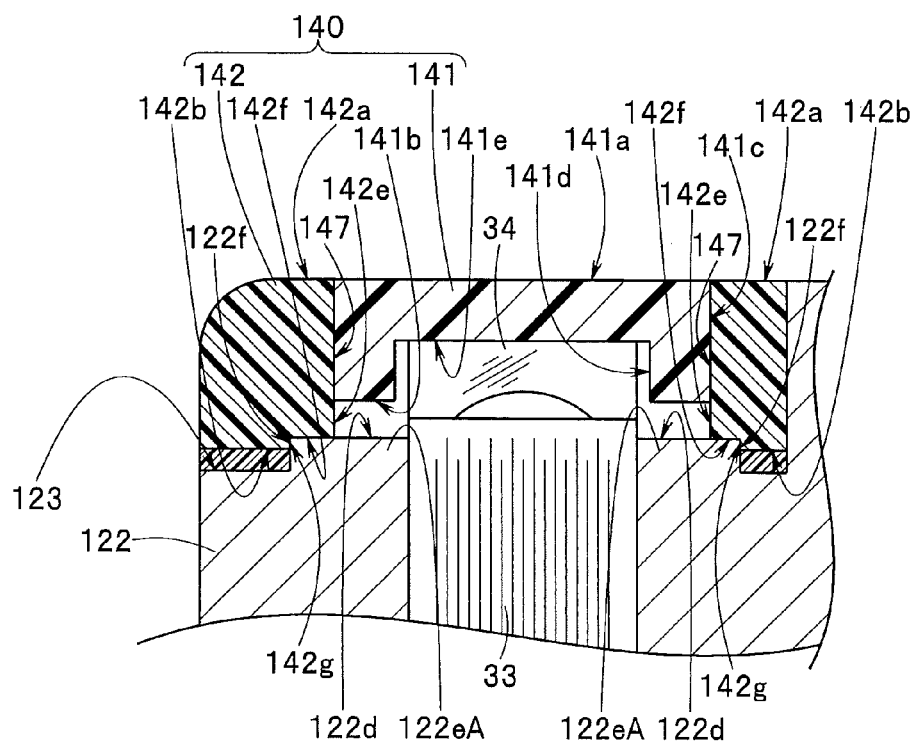
FIG. 17 is a diagram for explaining another configuration and action of the endoscope in which the convex portion side surface of the distal end rigid portion convex portion projecting from the distal end face adheres to the inner side surface of the distal end cover.

Note that, in the distal end rigid portion convex portion 122e shown in FIG. 16, the convex portion side surface 122f is arranged to be closely attached to the inner side surface 142e. However, as shown in FIG. 17, a convex portion disposing portion 142f may be formed on the inner side surface 142e side of the second proximal end face 142b of the second molded portion 142. The convex portion side surface 122f of the distal end rigid portion convex portion 122eA is arranged to be closely attached to a contact surface 142g of a convex portion disposing portion 142f. As a result, adhesion of the adhesive to the first proximal end face 141b is eliminated and occurrence of a crack on the boundary surface 147 due to the adhesive 29 is also eliminated.

In the embodiment explained above, the first molded portion 141 is formed in the columnar shape. However, the first molded portion 141 may be configured in a prism shape.

Note that, the present invention is not limited only to the embodiments explained above and can be variously modified without departing from the spirit of the invention.

What is claimed is:

1. An endoscope comprising:
   a distal end rigid portion configuring a distal end portion of an endoscope insertion portion and having an illuminating portion disposed therein configured to emit illumination light; and
   a distal end cover fixed to the distal end rigid portion and integrally molded to include a transparent first resin member and a colored second resin member, wherein
   the first resin member configures a first molded portion including:
      an illumination window forming portion which includes an incident surface on which the illumination light emitted from the illuminating portion is made incident and an emission surface from which the incident illumination light is emitted; and
      an eaves portion projecting from a side surface of the illumination window forming portion and including a first surface located on the emission surface side and separated from the emission surface to the incident surface side, and a second surface located on the incident surface side, and
   the second resin member configures a second molded portion forming a distal end cover external shape that covers, in a close contact state, the side surface of the illumination window forming portion, the first surface of the eaves portion, and the second surface of the eaves portion;
   wherein the first molded portion configured by the first resin member further includes a convex portion projecting from the second surface of the eaves portion, and the second molded portion configured by the second resin member further forms a distal end cover external shape that covers a side surface of the convex portion in a close contact state.

2. The endoscope according to claim 1, wherein, in the distal end cover, a distal end cover proximal end face, which is a surface opposed to the distal end rigid portion, forms an identical plane configured by an end face of the convex portion in the first molded portion and a proximal end face of the second molded portion provided to be closely attached to the side surface of the convex portion.

3. The endoscope according to claim 2, wherein
   the convex portion is provided such that an outer side surface of the convex portion and an inner side surface of the convex portion are separated from the side surface of the illumination window forming portion of the first molded portion, and
   a boundary surface between the first molded portion and the second molded portion is located directly under a distal end face in the distal end cover external shape configured by the second molded portion.

4. The endoscope according to claim 1, wherein the second molded portion is further closely attached to an end face of the convex portion, and a distal end cover proximal end face, which is a surface opposed to the distal end rigid portion, is configured by the second molded portion.

5. The endoscope according to claim 1, wherein the eaves portion is provided on all side surfaces of the illumination window forming portion.

6. An endoscope comprising:
   a distal end rigid portion configuring a distal end portion of an endoscope insertion portion and having an illuminating portion disposed therein configured to emit illumination light; and
   a distal end cover bonded and fixed to the distal end rigid portion and integrally molded to include a transparent first resin member and a colored second resin member, wherein
   the first resin member configures a first molded portion including:
      an illumination window forming portion which includes an incident surface on which the illumination light from the illuminating portion is made incident and an emission surface from which the incident illumination light is emitted; and
      a first concave portion provided on the incident surface side in the illumination window forming portion, in which the illuminating portion is arranged,
   the second resin member configures a second molded portion including:
      a portion covering a side surface of the illumination window forming portion;
      a proximal end face present in a position projecting with respect to an end face on the incident surface side of the first molded portion, the proximal end face being opposed to the distal end rigid portion; and
      a convex portion further projecting from the proximal end face, and
   the distal end rigid portion includes a second concave portion having a bottom surface opposed to an end face around the first concave portion in the first molded portion, the second concave portion functioning as an adhesive pool, on an inside of which the convex portion is arranged.

7. An endoscope comprising:
   a distal end rigid portion configuring a distal end portion of an endoscope insertion portion and having an illuminating portion disposed therein configured to emit illumination light; and
   a distal end cover bonded and fixed to the distal end rigid portion and integrally molded to include a transparent first resin member and a colored second resin member, wherein
   the first resin member configures a first molded portion including:
      an illumination window forming portion which includes an incident surface on which the illumination light is made incident from the illuminating portion and an emission surface from which the incident illumination light is emitted; and
      a first concave portion provided on the incident surface side in the illumination window forming portion, in which the illuminating portion is arranged,
   the second resin member configures a second molded portion including:
      a portion covering a side surface of the illumination window forming portion; and a proximal end face present in a position projecting with respect to an end face on the incident surface side of the first molded portion, the proximal end face being opposed to the distal end rigid portion, and the distal end rigid portion includes a convex portion projecting toward an end face around the first concave portion to arrange a distal end face in a position spaced apart from the end face around the first concave portion in the first molded portion, the convex portion preventing an adhesive from intruding into a boundary surface between the first molded portion and the second molded portion.

8. The endoscope according to claim 7, wherein the convex portion of the distal end rigid portion further projects toward the proximal end face of the second molded portion, and a convex portion disposing portion in which the distal end rigid portion side convex portion is arranged is provided on an inner side surface side of the proximal end face of the second molded portion.

* * * * *